(12) United States Patent
Pierce

(10) Patent No.: US 7,354,433 B2
(45) Date of Patent: *Apr. 8, 2008

(54) DISINFECTION, DESTRUCTION OF NEOPLASTIC GROWTH, AND STERILIZATION BY DIFFERENTIAL ABSORPTION OF ELECTROMAGNETIC ENERGY

(75) Inventor: Brian N. Pierce, Chico, CA (US)

(73) Assignee: Advanced Light Technologies, LLC, Chico, CA (US)

(*) Notice: Subject to any disclaimer, the term of this patent is extended or adjusted under 35 U.S.C. 154(b) by 60 days.

This patent is subject to a terminal disclaimer.

(21) Appl. No.: 10/789,948

(22) Filed: Feb. 26, 2004

(65) Prior Publication Data

US 2004/0236267 A1 Nov. 25, 2004

Related U.S. Application Data

(60) Provisional application No. 60/450,736, filed on Feb. 28, 2003.

(51) Int. Cl.
*A61B 18/18* (2006.01)
(52) U.S. Cl. .................. 606/9; 128/898; 606/2
(58) Field of Classification Search ............. 128/898; 606/9; 607/88–94
See application file for complete search history.

(56) References Cited

U.S. PATENT DOCUMENTS

| | | | |
|---|---|---|---|
| 2,051,057 A | 8/1936 | Pettit | |
| 2,312,368 A | 3/1943 | Smith | |
| 2,428,090 A | 9/1947 | Naeher et al. | |
| 2,485,660 A | 10/1949 | Robertson | |
| 3,494,724 A | 2/1970 | Gray | |
| 3,693,623 A * | 9/1972 | Harte et al. | 606/9 |
| 3,941,670 A | 3/1976 | Pratt, Jr. | |
| 4,015,341 A | 4/1977 | McKinney et al. | |
| 4,170,997 A | 10/1979 | Pinnow et al. | |
| 4,416,908 A | 11/1983 | McKinney et al. | |
| 4,469,098 A | 9/1984 | Davi | |
| 4,640,283 A | 2/1987 | Sawa et al. | |
| 4,672,969 A | 6/1987 | Dew | |
| 4,815,447 A * | 3/1989 | Mills | 600/1 |
| 4,815,448 A | 3/1989 | Mills | |
| 4,836,203 A | 6/1989 | Muller et al. | |
| 4,880,512 A | 11/1989 | Cornelius et al. | |
| 4,920,978 A | 5/1990 | Colvin | |

(Continued)

OTHER PUBLICATIONS

Dowell, Floyd E. et al.; "Automated Nondestructive Detection of Internal Insect Infestation of Wheat Kernels by Using Near-Infrared Reflectance Spectroscopy"; 1998, *J. Econ. Entomology*, vol. 91, No. 4, pp. 899-904.

(Continued)

*Primary Examiner*—Henry M. Johnson, III
(74) *Attorney, Agent, or Firm*—Townsend and Townsend and Crew LLP.; M. Henry Heines

(57) ABSTRACT

Neoplastic tissue, viral and bacterial infections, and other physiological disorders and conditions are treated by irradiation of the host with electromagnetic radiation at a wavelength that is differentially absorbed by the offending tissue or cells. Radiation with differential absorption is also used in the sterilization of articles and packing made from synthetic polymers and for the treatment of food stuffs.

5 Claims, 10 Drawing Sheets

U.S. PATENT DOCUMENTS

| | | | |
|---|---|---|---|
| 4,926,861 A | 5/1990 | Fenyo et al. | |
| 5,186,181 A | 2/1993 | Franconi et al. | |
| 5,197,470 A | 3/1993 | Helfer et al. | |
| 5,213,830 A | 5/1993 | Haagensen et al. | |
| 5,364,645 A | 11/1994 | Lagunas-Solar et al. | |
| 5,380,189 A | 1/1995 | Clary et al. | |
| 5,382,441 A | 1/1995 | Lentz et al. | |
| 5,413,800 A | 5/1995 | Bell et al. | |
| 5,504,366 A | 4/1996 | Weiss et al. | |
| 5,707,401 A | 1/1998 | Talmore | |
| 5,718,246 A * | 2/1998 | Vona | 128/898 |
| 5,759,200 A * | 6/1998 | Azar | 607/89 |
| 5,820,820 A | 10/1998 | Pierce | |
| 5,881,534 A | 3/1999 | Ahlqvist et al. | |
| 5,993,442 A | 11/1999 | Omori | |
| 6,011,889 A | 1/2000 | Daniel et al. | |
| 6,035,246 A | 3/2000 | Wagner | |
| 6,071,944 A * | 6/2000 | Rodgers et al. | 514/408 |
| 6,090,102 A | 7/2000 | Telfair et al. | |
| 6,104,959 A * | 8/2000 | Spertell | 607/101 |
| 6,106,521 A | 8/2000 | Blewett et al. | |
| 6,110,195 A | 8/2000 | Xie et al. | |
| 6,149,671 A | 11/2000 | Norquist et al. | |
| 6,162,213 A | 12/2000 | Stewart | |
| 6,267,779 B1 | 7/2001 | Gerdes | |
| 6,268,200 B1 | 7/2001 | Tucker et al. | |
| 6,290,712 B1 * | 9/2001 | Nordquist et al. | 607/88 |
| 2002/0002391 A1 | 1/2002 | Gerdes | |
| 2002/0051751 A1 * | 5/2002 | Mills | 424/9.361 |
| 2002/0173780 A1 * | 11/2002 | Altshuler et al. | 606/9 |
| 2004/0236267 A1 * | 11/2004 | Pierce | 604/20 |

OTHER PUBLICATIONS

Dowell, Floyd E. et al.; "Identifying Stored-Grain Insects Using Near-Infrared Spectroscopy"; 1998, *J. Econ. Entomology*, vol. 92, No. 1, pp. 165-169.

* cited by examiner

DISINFECTION, DESTRUCTION OF NEOPLASTIC GROWTH, AND STERILIZATION BY DIFFERENTIAL ABSORPTION OF ELECTROMAGNETIC ENERGY

CROSS-REFERENCE TO RELATED APPLICATION

This application is related to U.S. Provisional Patent Application No. 60/450,736, filed Feb. 28, 2003, and claims all benefits legally capable of being offered by the provisional patent application. The entire contents of the provisional patent application are incorporated herein by reference.

BACKGROUND OF THE INVENTION

The prolific use of synthetic chemicals, antibiotics, pesticides, and herbicides is of increasing concern to environmentalists, health care professionals, and the public at large as the scientific community gains a better understanding of the implications that these substances have for medicine, agriculture, and global society in general. Antibiotics and medicines are widely used for therapeutic purposes in treatments of a vast array of afflictions and infestations; chemicals and radiation are widely used on both humans and crops; insecticides are even used on children to kill head lice. While these treatments are useful and effective, there is increasing concern over the threats, both potential and actual, that the chemicals pose to the environment and to long-term human health.

A further concern in the use of chemical agents is the ability of the microbes, pathogens, bacteria and pests that are the targets of these agents to develop resistance to them. Agriculturists and physicians now believe that the typical chemical agent will have a life span of only five to ten years from its introduction before the target organism develops enough resistance to render the agent ineffective. Many of the most effective pesticides and herbicides are expected to lose their approval rating under the Food Protection Act and the Clean Air Act. These losses of effectiveness and approval rating have generated a sense of urgency among agriculturists around the world in their search for ways to remain competitive and to maintain their market share on an international basis.

SUMMARY OF THE INVENTION

It has now been discovered that electromagnetic radiation of a wavelength and flux density chosen to meet particular parameters is an effective treatment for a variety of afflictions and infestations, including the presence and growth of neoplastic tissue, of viral infections, and of conditions in general whose development and proliferation are mediated by enzyme activity or by other bio-reactive substances. The present invention thus resides in the identification of substances that occur in pathogenic material and are critical to its survival or proliferation, and the selective exposure of matter or organisms that are adversely affected by such pathogenic material to achieve beneficial results, including clinical therapy, sterilization, and in general the remediation of environmentally or physiologically unfavorable conditions. The matter or organism to be treated is thus subjected to electromagnetic radiation whose spectral properties reflect the spectral differences between the host material or organism and the offending substance or component of the host. The selective irradiation produces differential absorption that induces wavelength-dependent photochemical and/or photomechanical reactions that cause changes or quantum transitions to occur in the vibrational, rotational, magnetic, and/or electronic states of the molecules, producing a beneficial effect by means such as selective disinfection, denaturation, disruption, and/or dehydration. Photochemical reactions are those that are initiated or influenced by light, such as ultraviolet light, for example. Photomechanical reactions are light-induced reactions that arise from mechanical actions on a molecular scale such as bending, stretching, rocking, rotation, and vibration.

Among the many advantages that the present invention offers are the fact that both photochemical and photomechanical reactions are pollution-free, and that pests or pathogens cannot develop resistance to heat or to the absorption of electromagnetic radiation. Additionally, the invention does not require the investments of time and expense that are needed in discovering, screening, and registering new chemicals or drugs, and the invention is readily amenable to scale-up for commercial implementation. Since the invention can be performed without causing chemical changes to the host, the invention is well suited for organic applications as well as commercial applications. In many embodiments of the invention, the irradiation lacks sufficient energy to break a chemical bond and is insufficient to cause ionization.

The present invention thus resides in methods for killing neoplastic tissue in a living organism by the irradiation of the organism with electromagnetic radiation at a wavelength that is absorbed preferentially by the neoplastic tissue, and doing so at a sufficient intensity and for a sufficient period of time that the heat generated by the radiation destroys the neoplastic tissue without substantial injury to the surrounding tissues. The present invention also resides in methods for deactivating enzymes in living tissue, and thereby disrupting certain undesirable biological or physiological processes that rely on the activity of these enzymes, by irradiating the tissue with electromagnetic radiation at a wavelength that is absorbed preferentially by the enzymes, and doing so at a sufficient intensity and for a sufficient period of time to denature the enzymes. These undesirable biological or physiological processes include, but are not limited to, viral infestation or growth or any of the cellular processes that are mediated, disrupted, or blocked by viruses, including the immune response.

The invention further resides in methods for sterilizing objects or articles such as the medical devices and other equipment used in laboratory, clinical, or surgical procedures where sterile conditions are required. Such devices and equipment are frequently constructed of synthetic polymers and must be sterilized for re-use after having come in contact with biological material. In accordance with this invention, an article is sterilized to remove any glucose present in the article or on its surface by irradiating the article with electromagnetic radiation at a wavelength that is selectively absorbed by covalent O—H bonds without causing significant or substantial changes to the molecular structure of the synthetic polymer from which the article is constructed. Alternatively or in conjunction with glucose dehydration, proteinaceous matter is removed or decomposed by irradiation of the article with electromagnetic radiation at a wavelength that is selectively absorbed by covalent N—H bonds, again without causing significant or substantial changes to the molecular structure of the synthetic polymer. Alternatively or in conjunction with glucose dehydration and protein decomposition, further bio-reactive substances such as RNases, DNases, pyrogens, and nucleic acids in or on the article are decomposed or deactivated by irradiation with electromagnetic radiation at a wavelength that is selectively absorbed by these substances, again without causing significant or substantial changes to the molecular structure of the synthetic polymer. Still further targets, embodiments, objects, and applications of the invention will become apparent from the description that follows. All literature citations in this description are hereby incorporated herein by reference.

DETAILED DESCRIPTION OF THE INVENTION AND PREFERRED EMBODIMENTS

Figure 1:
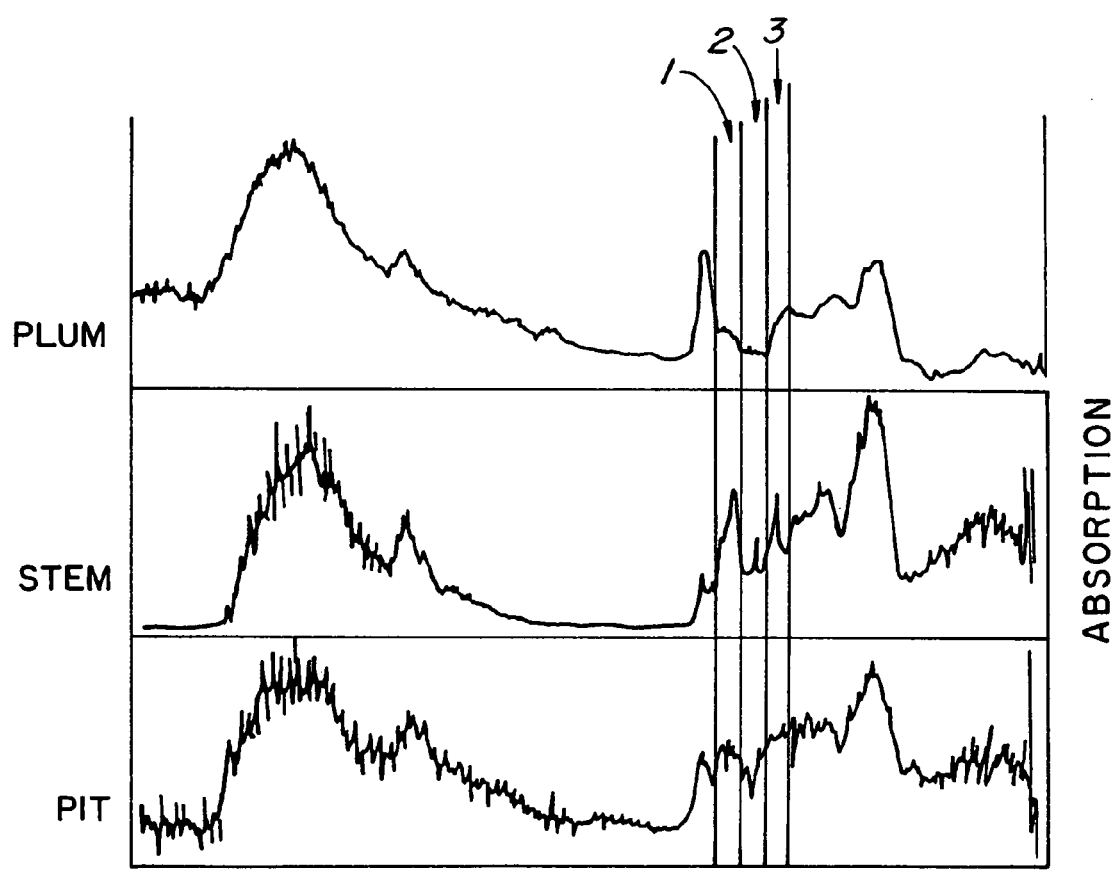
FIG. 1 is a combined chart showing three absorption spectra, representing the flesh, stem, and pit, respectively, of a plum.

One method for determining the parameters of the treatment of a given host, article or product (collectively referred to herein as the "host") in accordance with this invention involves analyzing the host as well as the associated target or infestation (collectively referred to herein as the "target") are analyzed to determine their spectral properties. The spectra are then compared, and the frequencies that exhibit the greatest difference in absorption between the host and the target, or at least those that exhibit a sufficient difference in absorption to permit selective absorption, are then identified. Once identified, these frequencies are evaluated for their availability, power conversion efficiency, available flux density, emission bandwidth, and efficiency after filtering or frequency modulation, as well as the transparency of the host to the frequencies. Flux density tests are then conducted to determine the maximum intensity that the host can withstand without suffering undesirable side effects or conversions. When the host is living or biological tissue, these tests are preferably performed in vivo, particularly in those cases where damage of the host is not objectionable, such as food items including grains, raw meat or fish, or non-food items such as paint. Otherwise, these tests can be performed in vitro. Flux density tests are also performed on the target. The difference in absorption and the parameters for processing are then established. Process time, for example, is determined by the magnitude of differential absorption, those with a large differential permitting very short process times provided that sources with high intensity and narrow band emission at the desired wavelength(s) are available. When the differential is low in magnitude, it is preferable to identify and determine appropriate parameters for several different wavelengths that can then be used simultaneously. Such multi-mode processing, i.e., multi-wavelength treatment, can include irradiation at any or all wavelengths that do not produce undesirable side effects in the host. The location of the target relative to the host, i.e., whether the target is embedded in the bulk of the host or concentrated on the surface of the host, is a further factor in the wavelength selection. If the target is embedded in the host, the wavelength must be one to which the host is at least partially transparent to permit the radiation to reach the target. For targets on the host surface, preferred wavelengths are those to which the host is reflective or at least nonabsorptive. The physical state of the host and the means by which the host is conveyed or exposed to the radiation source are further contributing factors in some cases.

Different types of spectra can be used in the identification of the appropriate wavelengths. Infrared spectroscopy, for example, can detect pathogens in grain on conveyer lines and IR monitoring systems are in commercial use for detecting insect infestations in grain bins.

Effects that can be achieved by differential absorption include destruction of microorganisms, disinfection or disinfestation, denaturation of proteinaceous matter, disruption of biological processes, and dehydration of carbohydrates and other substances. Disinfection or disinfestation is the ridding of the host of an infestation by killing or dislodging the pest or making the environment undesirable or intolerable for the infestation. Denaturation is the conversion of a protein by heat which renders the protein inactive. Dehydration is the selective reduction of the amount of water or solvent in the host or in a portion of the host, thereby depriving offending substances from their ability to survive. Sterilization is the removal or destruction of the viability of pathogens in the host that could cause disease or infection. Further effects that can be achieved are marking, tagging, or illuminating one or more of the offending substances to reference these substances for further targeting for action of a chemical agent, a catalyst, or a nanobot (i.e., a robot that performs functions on a nanometer scale).

Application of the present invention to the destruction of neoplastic tissue and cancer therapy in general operates through both general and specific modalities. For example, studies of structural changes in both malignant and normal DNA upon irradiation have revealed a high degree of differential at 265 nm, the malignant DNA absorbing the radiation to a degree about eighty times greater than the normal DNA. DNA is known to denature at temperatures in the range of about 75° C. to about 90° C. Cancers in general as well as specific types of cancer will require a delivery system and/or device that supplies the radiation to the cancer site in an amount sufficient to provide effective treatment. Treatment of a lesion on the skin surface, for example, can be achieved with a less sophisticated delivery system than a lesion or neoplastic tissue located deep inside the host will require. Nevertheless, delivery systems for all cancers with have certain common features, including a source, a means for energy or wavelength selection or optimization, means for conveying the radiation to the treatment site, and a system for controlling and monitoring the energy delivered to the site. Again, delivery systems for lesions on or near a body surface can be relatively simple since the primary and perhaps only requirements are that the radiation be focused and modulated to the appropriate flux density for effective treatment. Systems for delivery to deep tissue or other internal regions will require more elaborate means.

When irradiation is performed at wavelengths that are absorbed or scattered and thus do not penetrate the body, the treatment site can be reached by facilitating means such as fiber optics, lightpipes, or wave guides. Solid-core transmitting fiber optic devices are available that are formed from a variety of substrates including glass and crystalline materials such as heavy-metal fluorides, low-molecular-weight chalcogenides (such as for example $As_2S_3$), silver halides, sapphire, zinc silanide, synthetic diamond, and other liner and non-liner materials. Dielectric-coated metallic hollow waveguides can also be used. Highly flexible small-bore hollow wave guides are also available, with bore sizes ranging from 250 to 1,000 microns and consisting of metal and a dielectric coating deposited inside silica tubing. These are particularly useful for the delivery of infrared radiation. All of these systems are useful in the practice of this invention.

Energy and frequency optimization, and the use of both active and passive optical systems, are likewise useful in the practice of this invention, particularly in scanning and pulsing to expose a treatment site to the proper flux density for the optimum duration without allowing energy to dissipate to the surrounding tissue. Delivery systems that both monitor and control the frequency and flux density with mode lock, through feed-back and beam sampling and monitoring will further assure that collateral damage due to frequency shift or power fluctuation are minimized or avoided. Such systems have been developed by the telecommunications industry and are readily available for use in the practice of this invention.

Optically Induced Thermodynamic Reactions in Biological Matter

Organic compounds, particularly proteins, nucleic acids, polysaccharides, and lipids, contribute to many metabolic processes that are interdependent and complex and that are essential to the viability of cells and organisms. Interrupting or diminishing one or more of these functions will often result in the destruction of the cell or organism. Each of these compounds and the associated bonds are potential targets for the differential photochemical or photomechanical processing or treatment that occurs in the practice of this invention.

Proteins are of particular importance among organic compounds and are thus the focus of many treatments and processes of this invention. The amino acid sequence and the three-dimensional conformation of a protein are critical to the biochemical function of a protein and its interactions with biological systems. Alterations in the three-dimensional conformation can result in deactivation of the protein and prevention of its ability to take part in biochemical processes.

Some of the most important proteins are enzymes. Enzymes serve as catalysts to reactions occurring in biological systems and are therefore vital to metabolism. Enzymes are some of the most efficient catalysts known, increasing the rate of a reaction by a factor of up to 1,020. Enzymes are globular proteins.

The denaturation of a protein is any non-covalent change in the structure of the protein. Denaturation typically alters the secondary, tertiary or quaternary structure of the protein, causing the protein to lose its biological activity. Denaturation of an enzyme results in the loss of enzymatic activity. One cause of denaturation is heat, and depending on the protein and on the severity of the heating, the denaturation and loss of activity can be reversible or irreversible. As the temperature is raised, changes to the protein occur progressively. The first changes are to the long-range interactions that are needed to maintain the tertiary structure. The interactions are weakened and then broken, resulting in a more flexible structure and in greater exposure of the protein to solvent. With increased heating, the cooperative bonds or interactions that stabilize the structure are affected, allowing water to interact with the amide nitrogen atoms and carbonyl oxygen atoms and to form new hydrogen bonds. The increased access of water also weakens nearby hydrogen bonds by increasing the effective dielectric constant near those bonds. This results in the exposure of hydrophobic groups to the solvent.

The exposure of hydrophobic groups and new hydrogen bonding groups to the water results in an increase in the amount of water bound by the protein molecule, which causes the protein to unfold. This unfolding increases the hydrodynamic radius of the molecule which in turn increases the viscosity of the solution. The protein will then attempt to minimize its free energy by burying hydrophobic groups while exposing polar groups to the solvent. While this is analogous to the original folding that occurred when the protein was first formed, this new rearrangement occurs at a much higher temperature, which greatly weakens the short-range interactions that initially direct protein folding. The resulting structure is often vastly different from that of the native protein and therefore prevents the protein from performing its function.

As heat-denatured proteins are cooled, the molecules are frequently not in a conformation having the lowest free energy and tend to aggregate through hydrophobic bonds, which create kinetic barriers that prevent the molecules from returning to their native conformation. Before the protein can re-fold and return to its native conformation, these hydrophobic bonds would first have to be dissociated, an event that is energetically unfavorable because of the exposure of large number of hydrophobic groups on the protein to the solvent. This transformation of the protein to a form in which it cannot re-fold and therefore cannot perform its biological function is a desired effect in the disruption of the biochemical process that is integral to the development and proliferation of pathogens.

Polysaccharides, lipids, and lipopolysaccharides are further biological species whose function and activity can be eliminated in the practice of this invention. Certain microorganisms contain substances such as peptidoglycans and a glycocalyx that are not present in humans and other mammalian cell structures. These substances are thus useful as targets in the treatment of humans or mammalian tissue, skin or internal organs.

Peptidoglycans, for example, are common to most all cell wall structures of microorganisms. Glycan backbones consists of β-1,4 glycosidic bonds between N-acetylmuramic acid and N-acetylglucosamine. These acetyl linkages serve as effective target sites for infrared radiation since the array of amino acid residues in peptidoglycans is stabilized largely by bridging between glycan layers. In gram-positive organisms, these bridges link D-alanine residues to glycine residues, and in gram negative bacteria, these bridges link diaminopimelic acid to D-alanine. Gram-negative organisms contain an exterior layer that covers the thin peptidoglycan layer. This exterior layer contains lipopolysaccharides, inter-membrane proteins, and porins. Porins are a network of transport proteins that are critical to vital cell function. Porins can be deactivated by heat denaturation using infrared radiation. Lipopolysaccharides contain a tetra- or pentasaccharide end, keto-deoxyoctonate as a core polysaccharide, and the toxic lipid A head. The keto-deoxyoctonate is also an effective target for destruction by irradiation, particularly with infrared light, in accordance with this invention.

A glycocalyx is a viscous gelatinous polymer surrounding bacterial cells, and consists of polysaccharides, polypeptides, or both. When organized and firmly attached to the cell wall, the glycocalyx forms a capsule which contributes to bacterial virulence and protects pathogenic bacteria from phagocytosis by the cells of the host. A capsule can also help a bacterium become attached to any surface and survive in its natural environment. Bacteria that are not encapsulated are readily phagocytized and cannot cause disease. Destruction or weakening of a glycocalyx by irradiation that the glycocalyx selectively absorbs is therefore another effective means of treating bacterial infections in accordance with the present invention.

Teichoic Acids and Autolysins

The cell walls of many gram-positive bacteria contain teichoic acids. These acids are bonded to the peptidoglycan layers or to the plasma membrane and also assume a role in cell growth. Autolysins are enzymes that are essential to the growth of the cell wall. Teichoic acids regulate the activity of autolysins, preventing wall breakdown and lysis. The cell walls of acid-fast bacteria also contain peptidoglycan, and as much as 60% of the wall is lipids. Autolysins are therefore effective targets for radiative destruction by selective absorption in accordance with this invention as a means of sterilization of articles or the killing of bacteria in tissue.

A cell wall can also be damaged by exposing a lysozyme. Lysozymes are enzymes that catalyze the hydrolysis of the bonds between sugars in the polysaccharide chain and the peptidoglycan. Certain antibiotics, such as penicillin for example, destroy bacteria by interfering with the formation of the peptide cross bridges of peptidoglycan, thereby preventing the formation of a functional cell wall. The bond between the sugars is therefore another target site in the practice of the present invention, the destruction of the bond causing inhibition and breakdown of the peptide cross bridge, and thereby killing of the bacteria.

Endospores

When essential nutrients are depleted or when water is unavailable, certain gram-positive bacteria, such as *Clostridium* and *Bacillius*, for example, form specialized "resting" cells known as endospores. Endospores are dehydrated yet highly durable bodies. During sporulation or sporogenesis, a structure called a forespore is created, covered by a thick layer of peptidoglycan. A thick spore coat of proteins is then formed over the peptidoglycan as the outside membrane of the endospore. This protein coat is responsible for the resistance of the endospore to many harsh chemicals. Both the peptidoglycan layer and the outer protein coat are vulnerable to selective infrared absorption and therefore targets in the practice of this invention.

Once sporogenesis is completed, the endospore is depleted of most of its water and therefore cannot perform a metabolic function. The highly dehydrated endospore core contains DNA, small amounts of RNA, ribosomes, enzymes and small molecules that include a large amount of dipicolinic acid which is accompanied by a large calcium ion. These cellular components are essential for the resumption of metabolism in the bacterium. Germination begins with damage to the outer protein coat, and enzymes break down the remaining layers to let water in and allow metabolism to resume. The protein coat, the peptidoglycan, and the enzymes are therefore additional target sites in preventing the bacterium from germinating.

Arthropods and pathogens are related through their chitin-based structure, and the peptidoglycan layer is 50% chitin or its hydrolysis product N-acetyl-D-glucosamine. Preferential absorption of chitin in accordance with this invention is thus another means of killing the bacteria or rendering it inactive.

Infrared Targeting of Insects

The cuticle is of supreme importance in the survival of insects, as reported by Cohen, E., "Inhibition of chitin synthesis in insect systems," *Chitin in Nature and Technology*, Muzzarelli, R., et al., eds. (New York: Plenum Press, 1985). Since chitin is a major structural component of the cuticle, chitin is a target for preferential absorption in the practice of this invention in the control of insect pests. An insect can be targeted at several regions of its body that relate to the cuticle, chitin, or other material that exhibits differential absorption of electromagnetic energy such as infrared or microwave energy. The sensory structures of insets, for example, such as the compound eyes, the tympanic membranes, and antennae can be targeted to cause blindness or deafness, or to render the insect unable to navigate or to locate a mate.

It is known that insects exposed to infrared sources experience sensory difficulties without behavioral recognition of the light source. Upon exposure to a standard light source, insects respond and flee accordingly. Some insects are virtually blind to red wavelengths of light but are able to see far into the ultraviolet range, as reported by Wigglesworth, V. B., *Insect Physiology,* $8^{th}$ Ed. (London: Chapman and Hall, 1984). It has been inferred from these experimentally recorded phenomena that no red (visible light) receptor exists in such insects (for example, *Diptera*). See Menzel, R., "Colour receptors in insects" in Horridge, G. A., *The Compound Eye and Vision of Insects* (Oxford: Clarendon Press, 1975), and Kirschfeld, K., "The visual system of Musca: Studies on optics, structure and function," in Wehner, R., ed., *Information Processing in the Visual Systems of Arthropods* (Berlin: Springer-Verlag, 1972). According to Burkhardt, D., et al., "Electrophysiological studies on the eyes *Diptera*, Mecoptera and Hymenoptera," in *Information Processing in the Visual Systems of Arthropods*, Wehner, R., ed. (Berlin: Springer-Verlag, 1972), this "red blindness" is a result of the absence of pigments which screen for longer wavelength radiation. Insects do however possess a strong visual correlation between ultraviolet sensitive pigments and the spectral sensitivity maxima at 500, 450, or 350 nanometers; these pigments allow the insects to respond to the stray light spectral distribution of the sky. This is reported by Goldsmith, T. H. et al., "The visual system of insects," in Rockstein, M., *The Physiology of Insecta,* 2nd ed. Vol. 2. (New York: Academic Press, 1972), and Hamdorf, K., et al., "Photoreconversion of Invertebrate Visual Pigments," in *Information Processing in the Visual Systems of Arthropods*, Wehner, R., ed. (Berlin: Springer-Verlag, 1972). Insects have a greater visual response to natural, stray light rather than narrow bandwidths of radiation. In particular, when insects are exposed to stray light, they run, hop, jump or fly away. Accordingly, infrared wavelengths remain transparent (non-visible) to arthropods. The arthropod cornea is constructed of transparent cuticle, as reported by Dethier, V. G., *The Physiology of Insect Senses* (London: Methuen, 1963), and Land, M. F., "Mechanism of orientation and pattern recognition by jumping spiders (*Salticidae*)," in *Information Processing in the Visual Systems of Arthropods*, Wehner, R., ed. (Berlin: Springer-Verlag., 1972). The eyes of spiders and insects can thus be targeted by the process of the present invention. Infrared penetration of the cornea (or tympanic membrane) can disrupt visual (or auditory) function by the dehydration of the tissues, causing tissue damage before rehydration of the tissues occurs, the damage producing subsequent blindness (or desensitization), thereby making it difficult for treated insect to survive.

Additionally, antenna function and leg motility are related to the cuticle. Normally, the cuticle is sclerotized, making it drier, stiffer, and resistant to degradation via cross-linking in the protein-chitin, as reported by Busca, R. C., et al., *Invertebrates* (Sunderland: Sinauer Associates, 1990). In the joints, however, the cuticle is unsclerotized to allow for flexibility. This "weakness" means that IR exposure can change the ability of the internal chitin to retain water in tissues necessary for mobility, such as appendage muscle, connective tissue, and condyles (joint tissue); such changes can cause damage to insect joints, thereby disabling the insect.

Chitin as a Target

Microorganisms are classified into five kingdoms based upon three principal modes of nutrition. The kingdoms are the Monera (bacteria), Protista (principally algae and protozoa), Plantae (plants), Fungi (yeast and molds), and Animalia (nematodes-roundworms, platyhelminthes-tapeworms/flukes, and other phyla). The first two kingdoms are the foundation, out of which the remaining three have evolved. The nutritional modes upon which this system is based are Plantae (photosynthesis), Fungi (nutrient uptake by adsorption), and Animalia (nutrient uptake by ingestion). Additionally, non-cellular infectious agents, such as viruses (animal hosts), viroids (plant hosts), prions (infectious proteins), and virino (nucleic acid enclosed in host protein) constitute a microbial population which should also be included in the taxonomy. See Pelczar, Jr., M. J.; et al., *Microbiology: Concepts and Applications* (New York: McGraw-Hill, 1993).

Fungal chitin is chemically identical to the chitin of arthropods and is confined exclusively to the cell wall in all but one class where it can also be found as cytoplasmic inclusion granules. This is reported by Cohen, E., "Inhibition of chitin synthesis in insect systems," in *Chitin in Nature and Technology*, Muzzarelli, R., et al., eds. (New York: Plenum Press, 1985). In fungi, the role of chitin is to maintain cell wall shape and rigidity. The cell walls of fungi are composed principally of polysaccharides (sugars) and small amounts of lipids, proteins, and other inorganic ions. The polysaccharides are found in two major structures: threadlike microfibrils, and a less organized matrix. The structure of the microfibrils, the principle structural component of the cell wall, is that of separate polysaccharide chains wound about the others forming coarse, strong threads. These threads are embedded in the matrix, an aggregation of smaller polysaccharides that appears unstructured and granular. The matrix is also composed of proteins and lipids; these make up generally less than 10% and 8% of the matrix by weight, respectively. The fungal wall is analogous to reinforced concrete with the microfibrils acting as the steel rods and the matrix as the concrete. This is reported by Garraway, M. O. et al., *Fungal Nutrition and Physiology*. (New York: Wiley-Interscience, 1984).

The microfibrils themselves are composed of chitin, cellulose, or other noncellulose-based glucan. Structurally, chitin is an unbranched polymer of β-1,4-linked N-acetyl D-glucosamine units. The presence of chitin in the fungal cell walls of several of the major fungal groups is a distinguishing feature that sets fungi apart from higher plants. One basis of classification of fungi is the occurrence of matrix sugars and microfibrils since the carbohydrate distribution in the matrix differs from one taxonomic category of fungal groups to another. See Griffin, D. H., *Fungal Physiology* (New York: Wiley-Interscience, 1981).

The amount of chitin present (dry weight) in the fungal cell wall differs among the particular life cycle structures. The amount of chitin found in the sporangiophores (the spore forming fruiting body) in one species, *Mucor rouxii*, is 18% by dry weight. The cell wall of other fungi can contain as much as 39% to 58% chitin, also by dry weight. Phospholipids and sphingolipids are the major lipids found in fungal membranes; these lipids are polar molecules, which contain a hydrophilic "head" and a long hydrophobic "tail." The plasma membrane, which is the regulator of material passage from inside and outside of the cell, is composed of equal parts lipids and proteins, small amounts of carbohydrates, and in some cases nucleic acids.

In an *Aspergillus* sp. the amount of chitin increases within the cell wall just prior to germ tube emergence. Alterations in the concentration of cellular components, such as chitin, have been utilized as a way to determine fungal growth especially in assessing the growth of fungal plant pathogens. According to Griffin et al. cited above, controlling pathogenic fungi "through inhibition of chitin synthesis would seem to be an ideal mechanism for selective fungicides without deleterious side effects on the host. However, very few fungicides have been discovered with this kind of activity." Since chitin is IR active, the chitin (and therefore the cell walls) of fungi can be selectively disrupted in the practice of this invention by differential absorption of electromagnetic radiation of narrow bandwidths.

Another means of killing bacteria is by depriving them of mobility. This is achieved by denaturing proteins of the filament, flagella, and pili. Filament contains the globular protein flagellin which in most bacteria is not covered by a membrane. Flagellae are mechano-chemical biological motors that provide bacterial cells with the ability to alter speed and direction. Pili function similarly to glycocalyx by allowing bacterial cells to adhere to surfaces, including other cells, and thereby help bacteria to colonize. Disrupting the proteins in any of these structures will prevent bacteria from proliferating, and hence all of these structures are targets for differential absorption of electromechanical radiation in accordance with this invention.

Entry of the AIDS Virus into the Human Body

The preferred target of the AIDS virus is the human T-cell, which forms an essential part of the defense of the human body. When the virus attacks this cell, its SU protein attaches to CD4 receptor on the cell surface. The TM protein of the virus then penetrates the cell membrane and initiates a process of membrane fusion, which allows the core of the virus to enter the cell. Once the genetic material of the virus is in the cytoplasm of the cell, the process of producing DNA complementary to the viral RNA begins. The SU and TM proteins are therefore targets for the practice of the invention in treating an AIDS infection.

Other microorganisms that can be similarly controlled or eliminated by the present invention are yeast, mold (*Mucor, Aspergillus niger*), coliform, *E. coli, bacillus cereus*, Enterobacteriaceae, *Clostridium perfringens*, mesophilic anaerobes, *salmonella, lactobacillus*, and lysteria.

Furin as a Target

Furin is a cellular endoprotease that is a ubiquitously expressed 794-amino-acid type-1 transmembrane protein found in all vertebrates and many invertebrates. Its large lumenal/extracellular region has an overall homology with the same regions of other members of the proprotein convertase (PC) family, which belongs to the subtilisin superfamily of serine endoproteases. In addition to the signal peptide, which directs translocation of the pro-enzyme into the endoplasmic reticulum (ER), furin and the other PCs contain prodomains that are flanked by the signal peptidase cleavage site on the amino-terminal side and by a conserved set of basic amino acids that comprise the autoproteolytic cleavage site on the carboxyl-terminal side. This essential prodomain has a crucial role in the folding, activation and transport of PCs, and in the regulation of PC activity. Furin and the other PCs also share a conserved P domain, which is essential for enzyme activity and the modulation of pH and calcium requirements; this P domain is absent from the related bacterial enzymes. The furin cytoplasmic domain controls the localization and sorting of furin in the trans-Golgi network (TGN)/endosomal system, and furin is an important model for understanding the regulation of protein trafficking in mammalian cells.

Furin proteolytically activates large numbers of proprotein substrates in secretory pathway compartments, including pathogenic agents. Furin also has an essential role in embryogenesis, and catalyzes the maturation of a strikingly diverse collection of proprotein substrates. These range from growth factors and receptors to extracellular-matrix proteins and even other protease systems that control disease. As a result, furin plays a crucial role in many different cellular events and in diseases such as Alzheimer's, anthrax, bird flu, HIV, cancer, dementia and Ebola fever. In view of the structural and enzymatic properties of furin, its autoactivation, and its intracellular localization and trafficking, furin is a target for differential absorption of electromagnetic energy in accordance with this invention for the control of viruses and bacteria through furin inhibition. Furin is also a target for therapy of various cancers, since the increased levels of furin that are found in tumors correlate with an increase in the membrane-type matrix metalloproteinases, which are critical to rapid tumor growth and neovascularization.

Food Processing

The flavor and texture of foods are affected by the presence, amount and physical state of numerous chemical substances. Some of these substances are proteins, others are lipids and polysaccharides. When food is heated in processing all the components are heated at once, proteins unfold and denature, lipids oxidize and polysaccharides (sugars) break down or are caramelized.

An example of the change in flavors and textures in proteins is best referenced by the change in flavor of meat or eggs, which change during cooking as a result of protein denaturation. Lipids (fats and oils) also greatly affect the taste of food, and the oxidation rate of lipids doubles for every 20° C. rise in temperature. Upon oxidation, lipids become vulnerable to rancidity and develop an undesirable taste. Many of the more subtle tastes in food, which are attributed to essential oils, are lost as well.

Enzymes affect food in many ways, including the acceleration of undesirable processes such as decay, browning, and the development of off flavors. By the selective disabling of enzymes, these processes can be halted and food and its desirable flavors and shelf life can be preserved.

FIG. 1 shows three spectra, of which the uppermost is of plum flesh, the middle is of plum stem, and the bottom is of plum pit. The differences in these spectra in the mid IR range indicate wavelengths by which pits and stems can be detected, using either "If," "And," or "Not" logic, and either treated or excluded in several modalities. Distinct peaks can be detected by their higher absorption. Identification and rejection can be accomplished directly or enhanced with IR to tag for removal, or the pits and stems can be selectively heated for thermal scanning and removal. The four vertical lines that span each of the three spectra delineate three zones that are useful in differentiating the three materials. In Zone 1, the absorption in the stem and pits is considerably higher than the absorption in the plum flesh. Zone 2 likewise contains a distinct spike in the stem spectrum compared to a relatively low absorption in the flesh spectrum. Zone 3 likewise contains absorption in the stem and pit that are considerably higher than that in the flesh. Comparative spectra in any of these three zones can therefore be used in a process to remove both stems and pits.

Processing food with a differential photomechanical process allows for selective heating or the selective avoidance of heating a particular substance. This allows for the selective change in one substance and not another and can be used to change a flavor or to avoid a change in a flavor during processing.

Cancer Treatment

Infrared radiation at wavelengths that are absorbed to different degrees for proteins and lipids of neoplastic tissue as compared to proteins and lipids of normal tissue can be used in the practice of this invention to treat many types of cancer.

When molecular compositions of normal, benign and malignant skin lesions determined by infrared Fourier transform spectroscopy are compared, the following skin lesions show differences compared to normal and benign tissue: dermatofibroma, seborrhoeic keratosis, actinic keratosis, keratoacan thoma, basal cell carcinoma, squamous cell carcinoma, nevus intradermalis, nevus compositus, dysplastic nevus and lentigo maligna. The primary and secondary structure of the proteins is reflected by the amide vibrations of peptide bonds, first overtone at 1510-1610 nm, second overtone at 1040-1070 nm and the fundamental at 3006-3400 nm. The principal lipid vibrations were twisting and wagging ($CH_2$) and CH stretching vibrations of the second overtone at 2460-2540 nm and the fundamental at 3300-3600 nm.

Histologically distinguishable lesions show specific combinations of band changes indicating alterations in the protein configuration and in the molecular structure of the lipids. Histogenetically related lesions (actinic keratosis and sqamous cell carcinoma) produce similar but not identical patterns of spectral changes. Because the skin lesions produced reproducible and unique spectra, infrared radiation at selected wavelengths is useful in the practice of this invention for the treatment of skin lesions as well as many other types of cancer. Brain, prostate, breast, and other cancers have the same general metabolic requirements and composition as skin cancer, since the spectra show differences between malignant tissue and healthy tissue. This accounts for recent advancements in optical detection methods.

Whenever there is a sufficient amount of difference to detect cancer there is sufficient difference to treat cancer.

Sterilization of Articles Constructed of Synthetic Polymers

Synthetic polymers have a multitude of applications and uses, some of which, primarily those in the medical and food industries, require sterility. Products that are made from or packaged in synthetic polymers are typically sterilized by e-beam, gamma radiation, ethylene tri-oxide (ETO) or heat and then tested for pathogens, endotoxins, endonucleases and nucleic acids on a per lot basis. Current treatments of heat, gamma radiation and e-beam result in a temperature rise that leads to undesirable cross-linking and to structural changes that can embrittle and discolor material, reducing the tensile strength by ≦20%.

For many synthetic polymers, including some polypropylenes, Teflon, some silicones and other copolymers, these treatments are undesirable for further reasons. Gamma radiation, for example, creates hazardous waste, since the source must be "refueled" with cobalt-60 and requires extensive shielding which increases cost and manufacturing complexity. Treatments involving ETO exposure take 2-4 hours, produce noxious gases and require special packaging. Procedures involving heat treatment are limited by a low penetration depth and create a risk of deformation due to improper heating.

Different types and uses of polymers require different degrees of sterilization. Polymers primarily used for surgical equipment, implantable devices, and other sterile procedures in human or animal must be void of any viable pathogen, i.e., microbes, virus, or bacteria that could cause a disease or infection. The food industry likewise requires containers and equipment that are free from any viable pathogen that would cause illness or disease. Polymers used in biological testing require a higher degree of sterility. They must not only be void and free of any pathogen they must also be free of any reactive substance, i.e., they must be non-bio-reactive (NBR). The standard for NBR sterilization is to be free of RNase, DNase, pyrogens and nucleic acids. Endotoxins and pyrogens are particularly problematic. Endotoxins are lipopolysaccharides contained in gram positive microbial cell walls and, when liberated, cause aggressive immune responses in cells, which interfere with laboratory testing and research.

Photomechanical sterilization technology is very specific to chemical bonds and utilizes specific wavelengths to modify the target. The main structural component of polysaccharides and lipopolysaccharides is glucose which accounts for much of the cell walls. The decomposition of glucose by preferential absorption of electromagnetic energy in the practice of this invention is thus one means of achieving sterilization.

Biological test equipment is primarily made from one of three polymers—polyethylene, polystyrene and polypropylene. These polymers do not have an oxygen-hydrogen (O—H) bond, such as the one that is found in glucose, which will actively absorb energy in the infrared. The O—H bond thus present a target for selective absorption of electromagnetic energy. Irradiation directed to the absorption band of the O—H bond excites and drives off the OH group from the molecule, causing dehydration of the glucose. This will in effect kill any living organism, alleviating endotoxin or pyrogen contamination. Since nucleic acids have a constant chain of saccharide-phosphate bonds that constitute a backbone for the molecule, nucleic acids would also be affected by this irradiation. O—H bonds absorb radiation in the visible region and are responsible for the blue color of water and ice, O—H bonds absorb in the near infrared are 1450, 1935 nm. The mid infrared absorption for O—H bonds is 3500, 1600, 900, 500 cm-1. N—H bonds absorb in the near infrared at 1200, 1450, 1750, 2100, 2200 nm. The mid infrared absorption are 3700-3000, 1650-1500, 900-700 cm-1.

Figure 2:
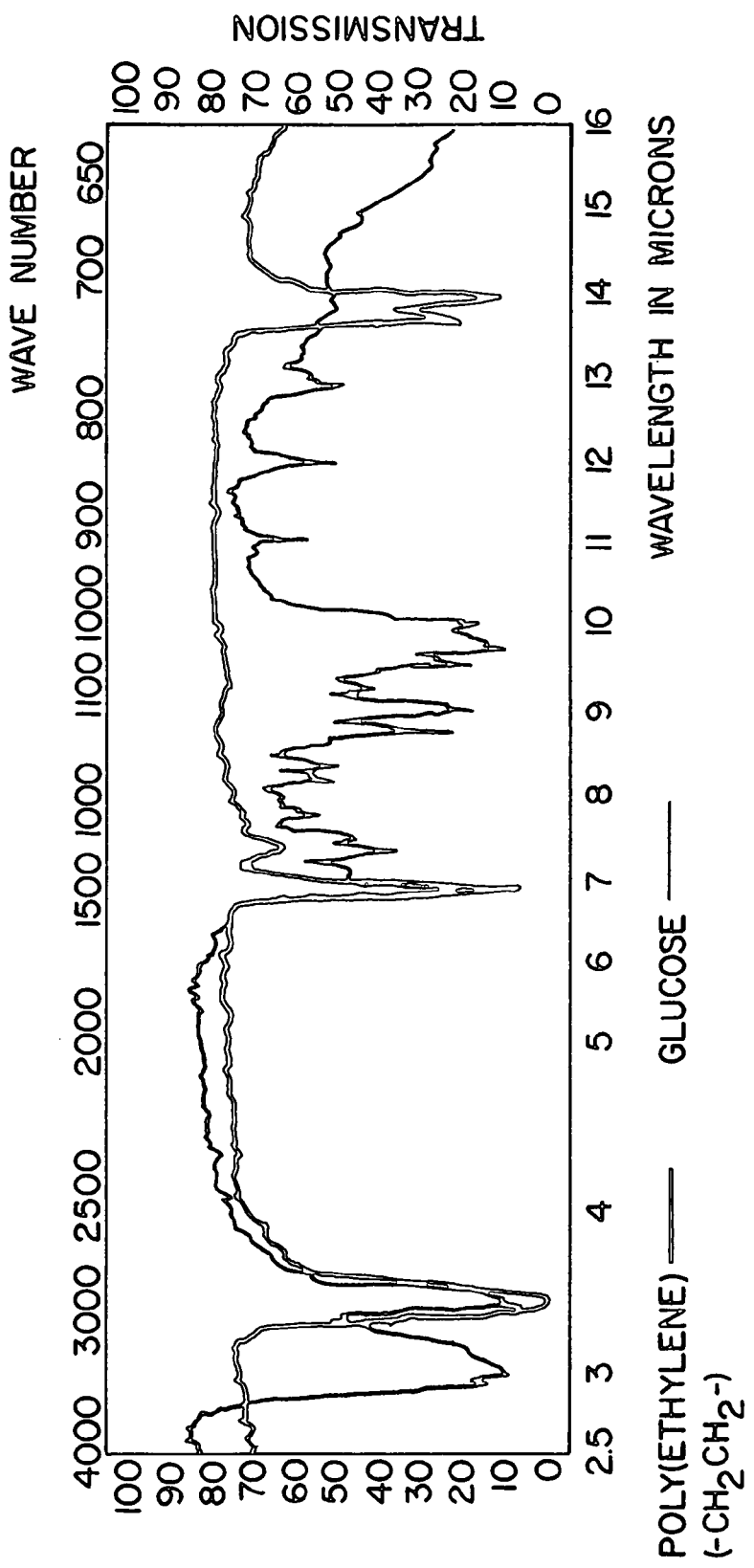
FIG. 2 is a chart showing an absorption spectrum of glucose superimposed over an absorption spectrum of low-density polyethylene.

Glucose, the target for the sterilization of many synthetic polymers, exhibits absorption differentials are wavelengths in many regions, with preferred wavelengths in the UV-VIS, NIR, fundamental and fingerprint regions. FIG. 2 shows the spectra of low-density polyethylene and glucose. The polyethylene exhibits strong absorption from 3.3μ to 3.5μ, and also from 6.8μ to 7μ and from 13.7μ to 14μ. The polyethylene is relatively transparent (70 to 80%) to all other wavelengths in the mid-IR range. Glucose has strong absorption from 2.8μ to 3.3μ due to the OH bond and also from 3.3μ to 3.5μ due to the CH bond. In the fingerprint region, glucose absorption occurs within the range of from 6.5μ to 10.5μ at 90 to 60% (6.5μ to 10.5μ transmission with only three small peaks at 11μ, 12μ and 13μ.) This indicates that selective glucose destruction can be achieved at wavelengths of from 2.8μ to 3.5μ and from 6.5μ through 13μ with only a low degree of heating of the polymer. Preferred treatment ranges for selectively heating glucose are 2.5μ to 3.3μ and 8.5μ to 10.5μ. A suitable radiation source for selective heating is a gray body emitter that emits in the vicinity of 3μ and a CO laser that emits in the 9-11μ range.

There are many useful targets (bonds that preferentially absorb particular wavelengths) for polymer sterilization, and appropriate targets can be selected for particular polymers. Silicone, for example, has OH bonds which are otherwise a prime target for sterilization. To avoid destruction of the silicone, the bond between nitrogen and hydrogen (NH) can serve as the target when seeking to decompose proteins and peptides.

Synthetic polymers are typically tested on a per-lot basis for pathogens or reactive substances. This testing most often requires two weeks, and shipments must be held until verifications are completed. With the practice of the present invention, validation can be performed on-line by monitoring the host polymer temperature during treatment and at the exit from treatment zone. The differential absorption process can be arranged for example to cause the target bio-load to reach a critical temperature of 150° C. while the host polymer temperature is maintained at 70° C. The absorbed energy can be determined by the following relation:

$$\frac{P}{A} \times t \times (A_\lambda) = E_a = m_1 \times C \times (T_c - T_\alpha)$$

where:
P=power
A=area
t=time
$A_\lambda$=absorption factor, i.e., the absorption derived from spectra (wavelength-dependent)
$E_a$=energy absorbed
$m_1$=mass of substance
C=heat capacity
$T_c$=critical temperature (the desired effect)
$T_\alpha$=ambient temperature The difference in absorption and the resulting differential heating allow one to determine the temperature of the target by monitoring the temperature of the host. If the host temperature is 70° C. the target pathogen temperature has reached critical temperature of 150° C. and the desired effect is achieved.

The food and beverage industry uses the same three polymers for packaging that are used in the medical device industry, and the same sterilization methods. The processes most commonly used for sterilizing food containers, bottles, lids and caps are thermal processes. In these processes, the bottles are hot-filled with a liquid in a hot-fill bottling line at a temperature high enough to kill any viable pathogens on the cap or bottle surface. The bottle is either over-filled with the liquid, or filled, capped, and inverted for a period of time long enough to expose the surfaces to the hot liquid to achieve thermal sterilization. This process and the required equipment are expensive and difficult to validate and involve a high usage of consumables. E-beam ETO and gamma radiation are also used but are often not cost-effective and raise toxic waste concerns.

Utilization of differential electromagnetic absorption in accordance with the present invention provides selective heating of the target pathogen and shorter exposure times. The short exposure times permit treatment at conveyer speeds of approximately 900 units per minute or more. Containers that are constructed entirely from polymers can be treated after filling, eliminating the opportunity for reintroduction of pathogens.

Active Re-Emission Spectroscopy

Heated bodies emit electromagnetic waves over a wide spectral range. Some of the radiation falls in the infrared region and is often called thermal or heat radiation. IR energy is emitted from all bodies at every temperature above absolute zero. Thermal radiation exists everywhere and permeates the space between bodies and within bodies.

In the practice of this invention, electromagnetic energy of a specific wavelength or focused wavelength band, and at a high enough flux density, is directed to matter or tissue, whether human, animal, plant, bacterial, viral or chemical, to cause the matter or tissue to re-emit energy of a wavelength different from that of the source. Exposing a substance to electromagnetic energy of a specific wavelength will cause some of the energy to be reflected, some absorbed, and some transmitted. The relative amounts of each are dependent on the chemical composition of the exposed matter. The wavelength of the reflected energy will be the same as that of the source. The energy that is emitted as a consequence of thermal agitation of the molecules and atoms of the target is thermal radiation and its emission wavelength varies with temperature.

While reflected energy can be detected, it is often scattered and difficult to analyze, especially when the reflecting body is moving, as in the case of processing lines. Emitted thermal energy can also be detected and can aid in the identification of a specific substance or foreign material. Signals from both reflected and thermal energy can be combined and logically analyzed to significantly increase the accuracy of detection. Combining reflectance-generated signals with thermal imaging therefore permits data comparison and can reduce the occurrence of false positive readings.

In the practice of this invention, organic tissue, such as dried fruit or meat for example, is irradiated with electromagnetic energy at a selected wavelength and the resulting emission is used as a means of detecting and identifying foreign matter, pits, stems, shell fragments, bone, pathogens, or any toxic substance present in the tissue. Each of these undesirable components will have a characteristic absorption and reflectance. The absorbed energy will cause heating which will result in thermal emission. The presence and identity of any of these components can be determined by a combination of reflectance spectroscopy and thermal emission analyses.

It is known that matter or an organism can be irradiated with short-wave ultraviolet radiation to cause the matter or organism to fluoresce or to emit visible light. Fluorescence can be detected and is used as a means of identification in accordance with procedures well known in the art.

Full Spectrum Analysis and Treatment

A method of full spectrum analysis and treatment of matter using electromagnetic energy in all non-ionizing frequencies or wavelengths illustrates how the principles of this invention can be implemented in a wide range of applications. In analysis and treatment, water is particularly illustrative in regard to wavelengths longer than about 10 electron volts (approximately 180 nm) due to absorption bands that appear in the UV-visible, infrared, and radio bands.

With even the shortest wavelengths of non-ionizing, ultraviolet spectroscopy, analysis and comparison leads to effective therapeutic and sterilization uses. Differential absorptions and emissions occur in both visible light and near-infrared. Near infrared emissions are particularly useful when analyzing or treating the human body, and regions of the near infrared are frequently referred to as the therapeutic window. This window starts at about 800 nm and extends to about 2500 nm. This range of frequencies includes first, second and third overtone absorptions. The fundamental and strongest absorptions takes place in the middle infrared (mid-IR) frequencies. Absorption spectra in the mid-IR range are used primarily in investigative, spectroscopic identification processes containing the fingerprint region. Water also has its fundamental absorption in the mid-IR and will therefore interfere with some spectroscopic methods and processes.

Water can be removed from samples and scans run to reveal details hidden in the overlap of O—H absorption bands. These bands may not be useful for all treatments but will reveal data useful for evaluation of overtones and undertones in the near infrared. Many samples are separated into their components and scanned separately to reveal a true differential for each component. The far infrared range is for the most part obscured by large bands of water absorption. Several small windows are present around 20 µm however, and other windows are present in the range of 1000 µm. Certain gigahertz (GHz) and terahertz (THz) frequencies, including those in the 200-500 GHz (0.2-0.05 THz) range, are also useful windows. At 230 GHz, for example, the transmission from malignant tissue is approximately 18%, while the transmission from normal tissue at the same frequency is approximately 60%, presenting a difference of 42%. The megahertz (MHz), kilohertz (KHz) and hertz (Hz) regions offer bands that are free from water absorption, although less defined. Absorption in the 3 Mhz range is particularly useful. Use of the full range of non-ionizing frequencies is frequently more effective and therefore preferable to the use of but a single point in the spectrum. Reaction patterns appear in a full-range analysis and the manner in which a substance reacts in one band of frequencies often leads to information as to how the substance will react in a different band.

The state of the art regarding spectral analyses of agricultural products, insects and microbes offers enormous amounts of valuable information including details regarding the processing of tissues and materials. Insects are an effective model for human tissue in view of the multiple layers and substances in insect bodies, and the presence in the regions of all or most of the same chemical bonds that are present in humans. Investigations into the effect of electromagnetic energy on the complex respiratory, optical, reproductive, nervous and cardiovascular systems of insects provide insights and avenues for achieving effective treatments in humans and allow testing to be performed on an expendable host. An O—H or a C—H bond responds to electromagnetic energy in mostly the same manner for human, vegetable or pathogen.

Figure 3:
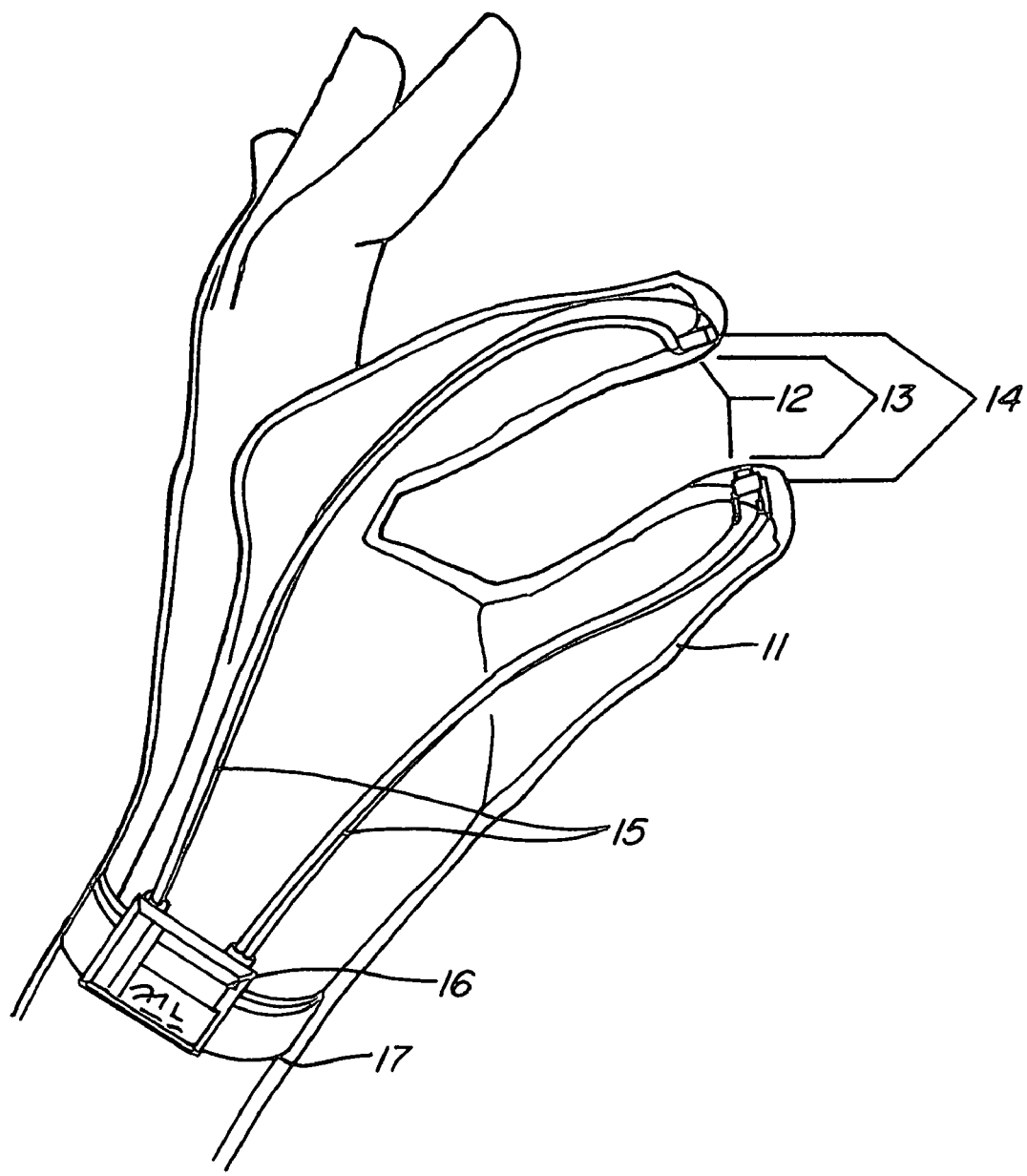
FIG. 3 is a drawing of a medical device in the form of a glove, shown worn by the hand of a physician, for use in the practice of certain embodiments of the invention.

FIG. 3 illustrates a spectroscopic glove-like device that can be worn on the hand of a physician. This glove-like device can be formed from medical grade silicone or other material suitable for surgical gloves and similar devices. This device can be equipped to function as both a detecting device, an analytic device, a therapeutic (e.g., radiation delivery) device, or a device serving a combination of these functions. The device can thus be useful in testing for and treating cancer. Portions of the source, means for monitoring energy and wavelength energy optimization, means for controlling the frequency, means for conveying energy to the treatment site, a thermal scan monitor, a beam sampler and a system for controlling and monitoring energy output can be carried by the glove-like device and connected to a central processing and control unit and associated hardware by cables or fiber optics.

The glove-like device 11 contains a pair of interlace couplings 12 located on the fingertips of the glove. These couplings form a lens system that detects bidirectional data coaxially from one point. A pair of miniature receiver/detectors 13 are also located near the tips of the fingers to function as a transition spectrophotometer. When the glove is used for cancer detection, the miniature receivers and detectors 13 are connected to the output couplings to generate a combined signal that allows for reflection and transmission of the light energy through a pair of fiber optical couplings 14. Electrooptical leads 15 extend from the components in the fingertips to a transmitter/processor/controller unit 16 that passes through the wristband 17 of the glove and from there to a power source (not shown). The transmitter/processor/controller unit 16 optically analyzes the signals from the receiver/detectors 13 while allowing the physician to manipulate the detection and delivery components to direct them to the precise area of the body where detection and treatment are needed.

Figure 4:
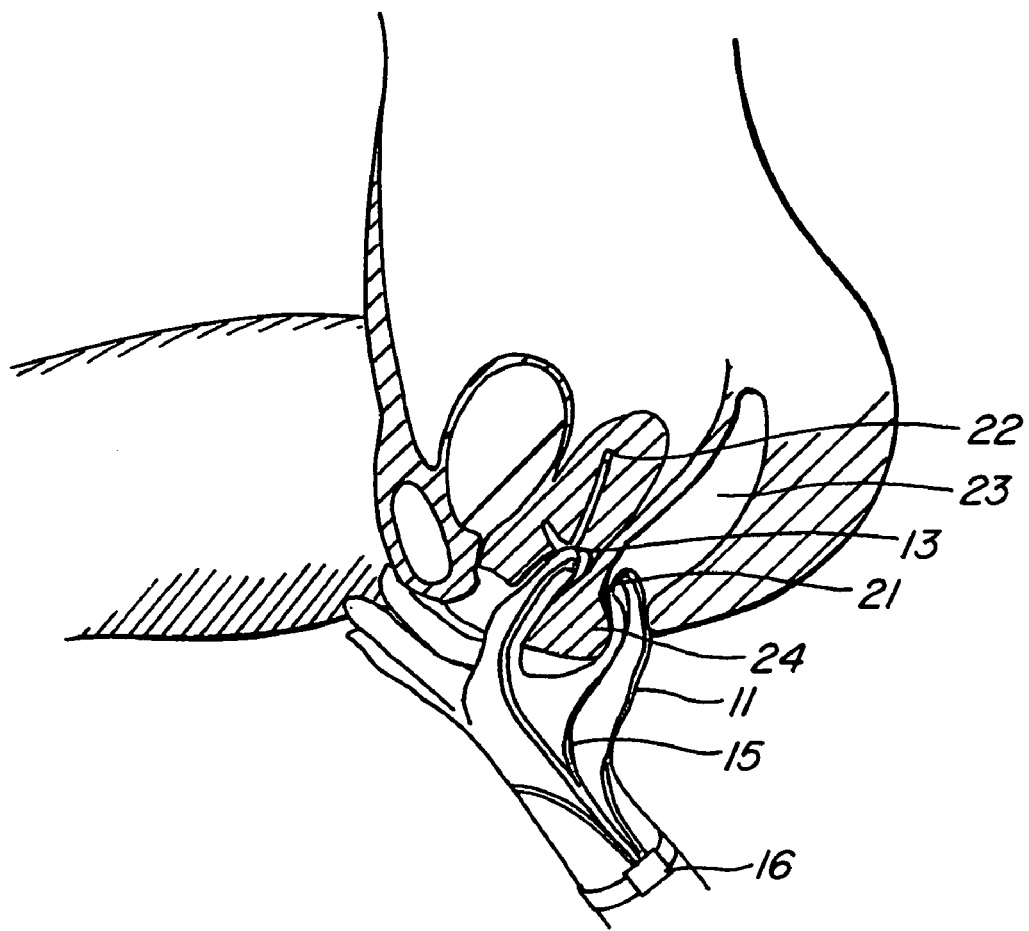
FIG. 4 is a cross section showing use of the device of FIG. 3 on a female patient.

FIG. 4 is a shows the device of FIG. 3 in use to test for cancer in the vaginal area of a female patient. One finger of the glove 11 is inserted in the vagina 21 toward the uterus 22 and a second finger is inserted in the rectum 23, such that the tips of the two fingers reside on opposite sides of the pelvic tissue 24. The receiver/detectors 13 in the tips of the two fingers receive and send signals to the transmitter/processor/controller unit 16 through the electrooptical leads 15. Malignant tissue is detected on the monitor due to the presence of a characteristic wavelength of the malignant tissue. Once malignant tissue has been detected, emitters can be attached to the glove-like device, or the device can be replaced by a second glove-like device to which emitters are already secured. In either case, the emitters will be those that emit radiation of a wavelength that will selectively destroy the malignant tissue without harm to the patient's normal tissue. By using the glove-like device, the radiation can be directed to the immediate area where the malignancy has been detected and the cancer can be treated without surgery.

Figure 5:
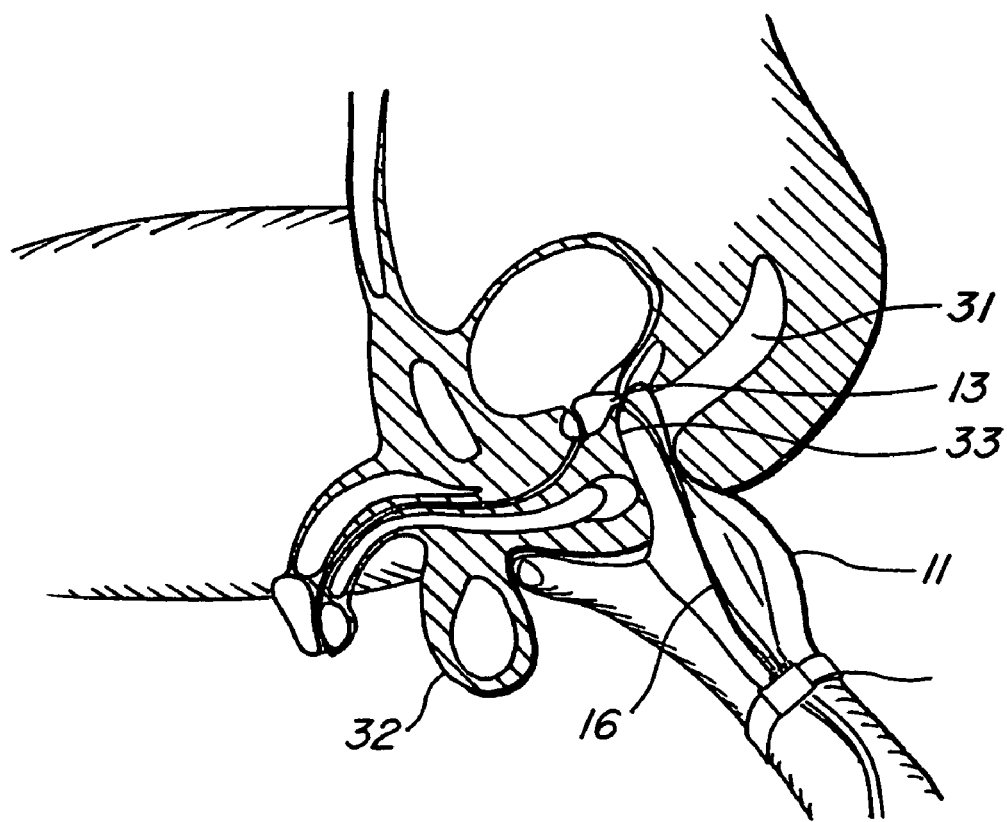
FIG. 5 is a cross section showing use of the device of FIG. 3 on a male patient.

The glove-like device of FIG. 3 is again shown in FIG. 5 where it is being used to test and/or to treat the prostrate gland of a male patient. In this case, one finger of the glove 11 is inserted in the rectum 31 of the patient while another finger is placed behind the scrotum 32. Here again, the receiver/detectors 13 in the tips of the two fingers receive and send signals to the transmitter/processor/controller unit 16 through the electrooptical leads 15. Cancer in the prostate gland 33 can thus be detected and treated in the manner set forth above in the description of FIG. 4.

Figure 6:
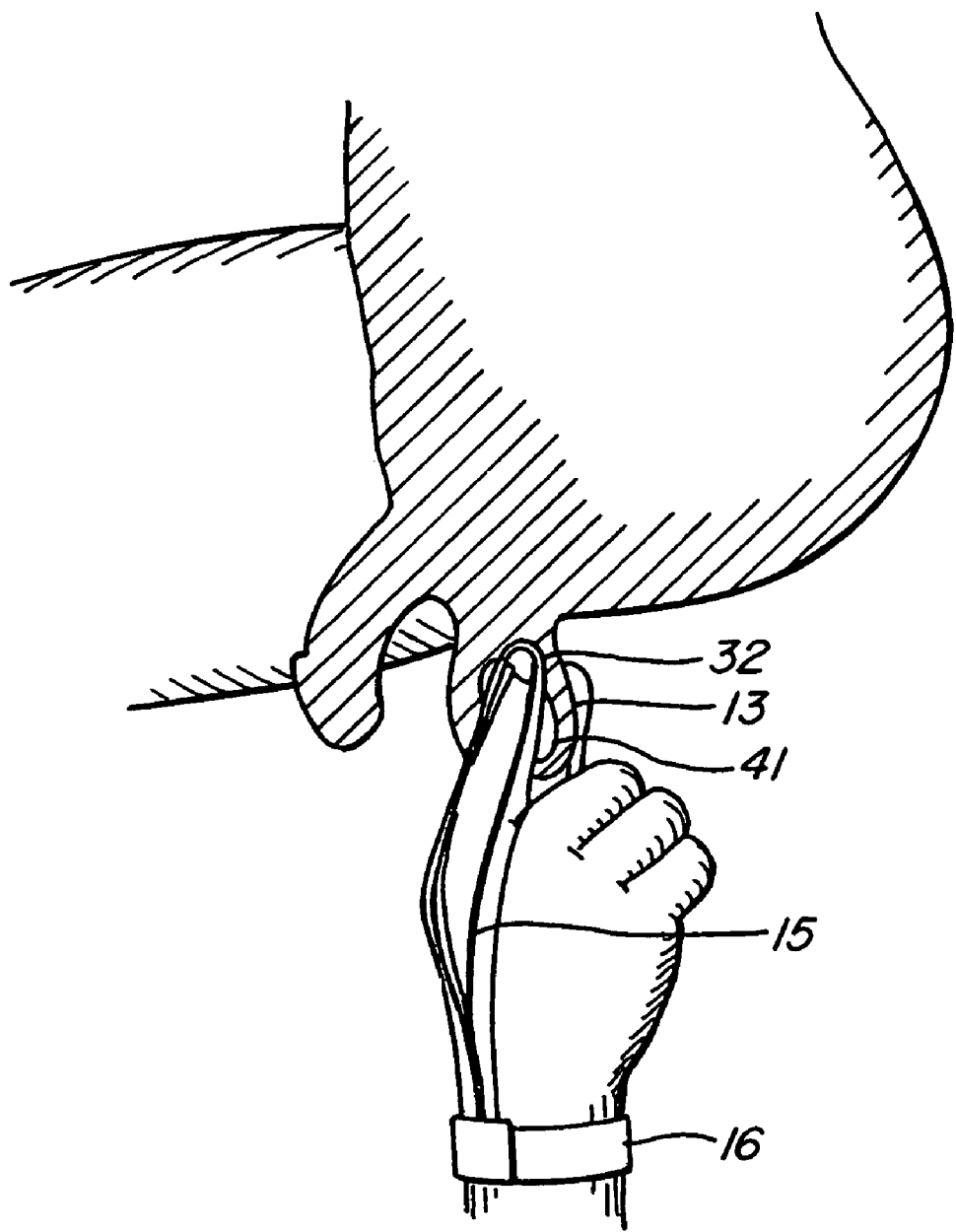
FIG. 6 is a cross section showing a further use of the device of FIG. 3 on a male patient.

In FIG. 6 the same device is shown in use for testing or treatment of cancer in a testicle 41 of a male patient. In this procedure, the thumb and forefinger of the glove-like device are placed on opposite sides of the patient's testicle 41, and the receiver/detectors 13 at the tips of the fingers send signals to the transmitter/processor/controller unit 16 through the electrooptical leads 15. Cancer in the testicle 41 can thus be detected and treated in the manner set forth above in the descriptions of the preceding Figures.

Figure 7:
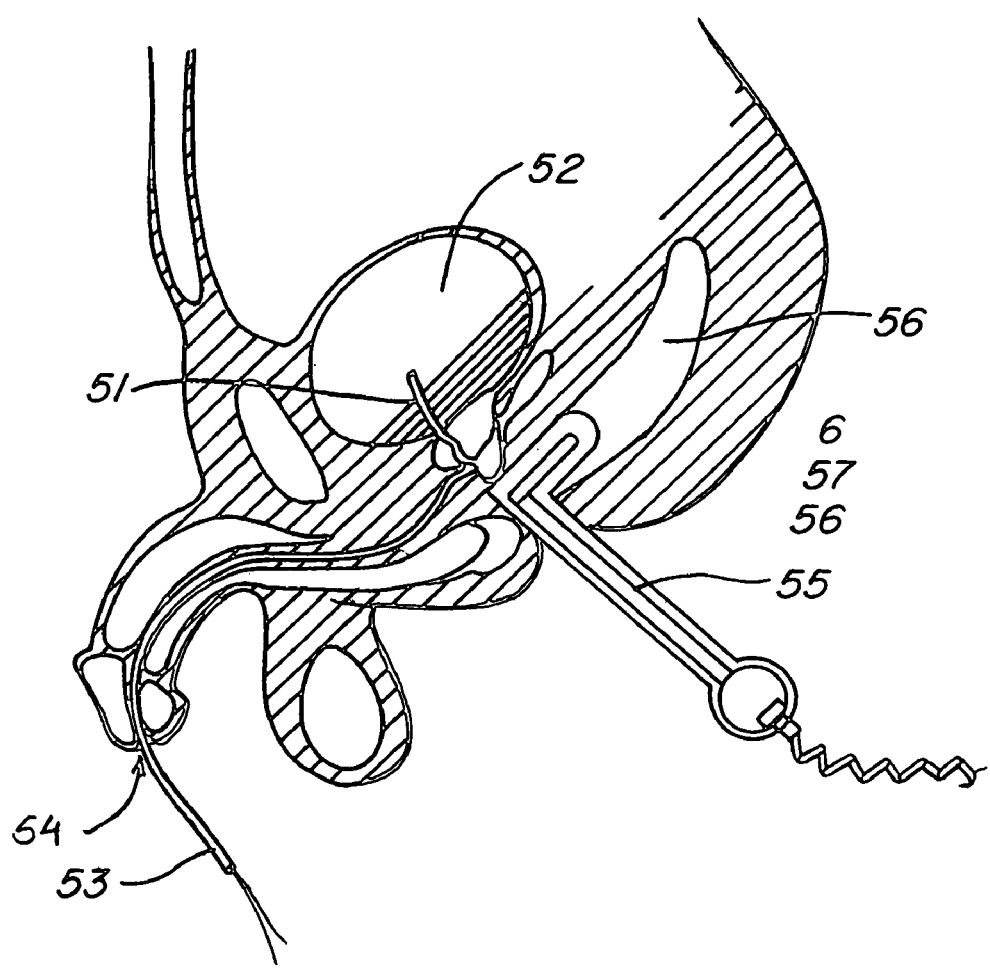
FIG. 7 is a cross section showing a further medical device useful in the practice of this invention, in use on a male patient.

FIG. 7 depicts a device that operates at a higher power level than that attainable with the glove-like device of FIG. 3. The device in FIG. 7 is shown in use for the treatment of neoplastic tissues present in the prostate of a male patient. A scattered light detector 51 is placed in the bladder 52 of the patient through a catheter 53 that is inserted in the urethra 54. An analytical and therapeutic optical wand 55 with an optical head 56 and a detector array 57 on the optical head is placed in the rectum 58. The bladder is filled with a reflective fluid that enhances the detection sensitivity of the optical wand 55 by reflecting the signal from the optical head 56 to the detector array 57.

Figure 8A:
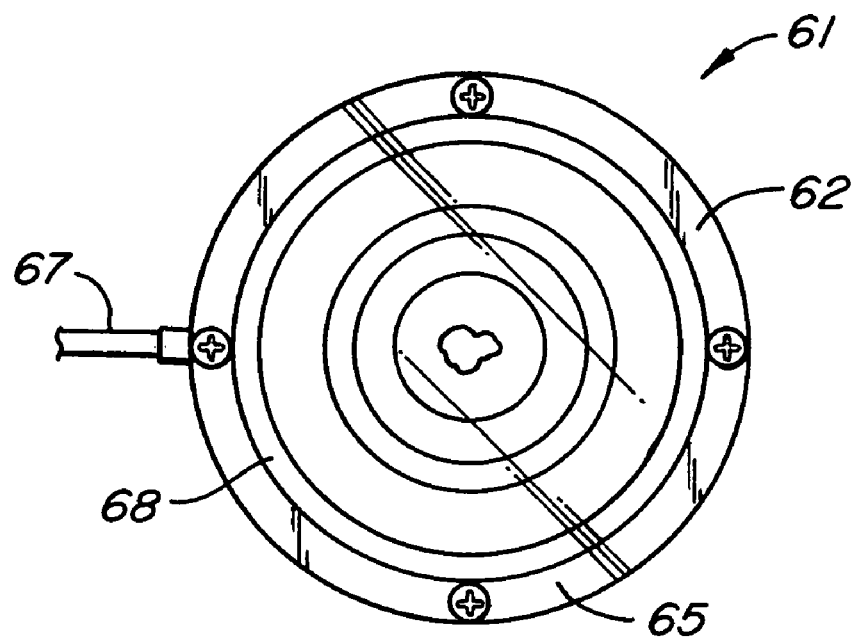
FIG. 8A is a top view of a device useful in testing a sample as part of the practice of this invention in certain embodiments.
Figure 8B:
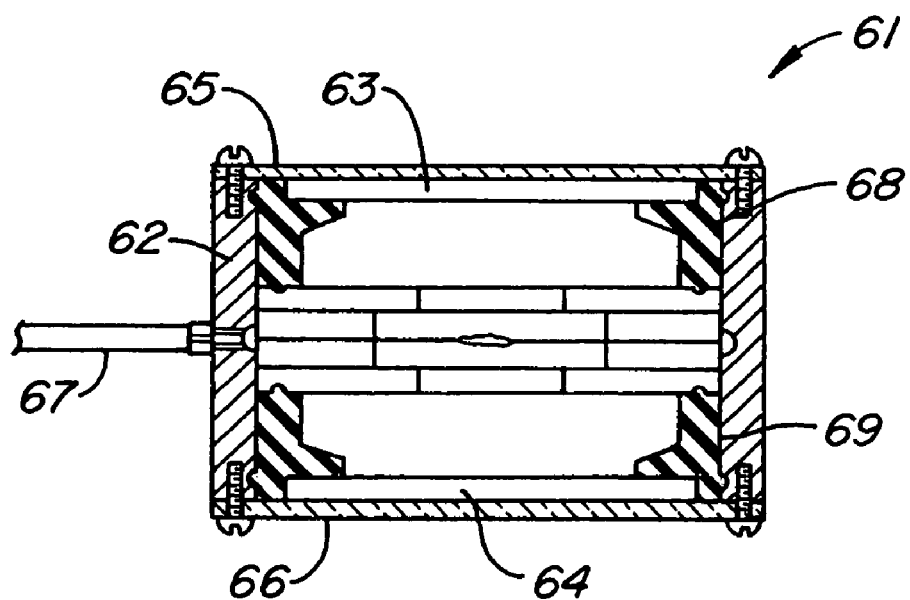
FIG. 8B is a side cross section of the device of FIG. 8A.

FIGS. 8A and 8B are top and side views, respectively, of a sample holder 61 designed to hold a sectioned sample for high-power laser spectroscopy and destructive radiation and to place the sample in controlled atmospheric conditions. The sample holder 61 can be mounted to a camera or a detector array enabling the direct transmission of radiation by laser for spectroscopic or thermographic analysis and imaging. The holder consists of a cylindrical housing 62 closed at its two ends by optical filter windows 63, 64 held in place by clamping disks 65, 66 and fitted with a vacuum line 67. Spacers 68, 69 and a series of transparent sample support disks 70 support the sample in the center of the housing. The optical filter windows 63, 64 transmit light of the selected wavelength.

Figure 9:
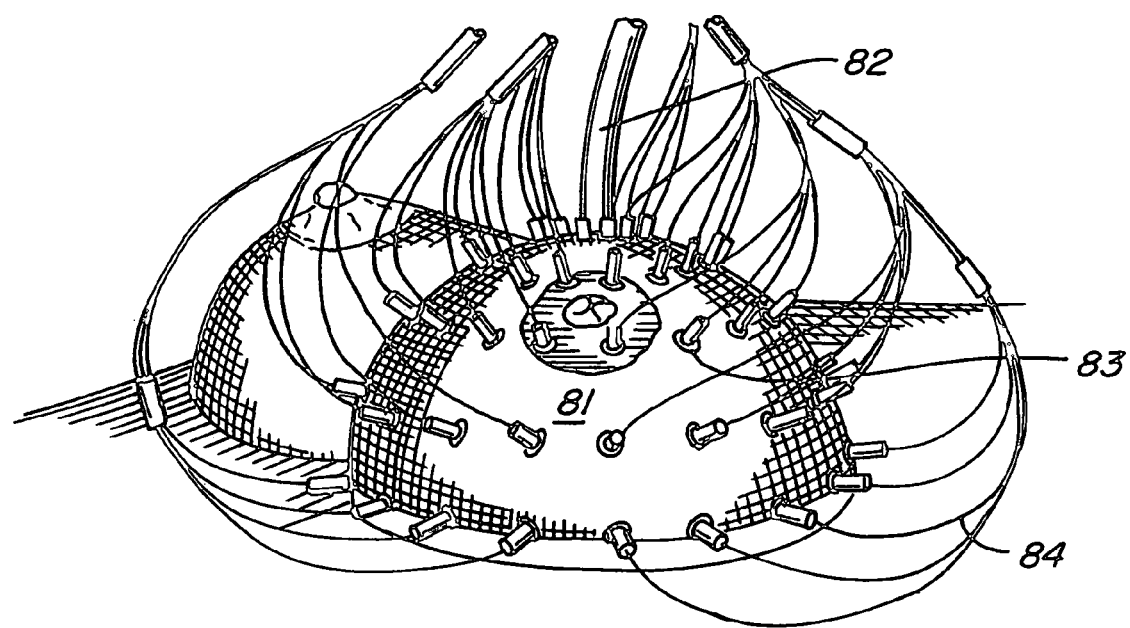
FIG. 9 is a perspective view showing the performance of a test for breast cancer according to certain embodiments of the invention.

FIG. 9 is a perspective view of the breasts of a female patient, one of which has been fitted with a detection and treatment device in accordance with the present invention. The device includes a cup 81 of transparent polymer that is secured to the surface of the breast by a low vacuum applied through a series of vacuum lines 82. Attached to the underside of the cup are a series of pairs of input/output couplings 83, each of which includes a receiver/detector that serves as a transmission spectrophotometer. Electrooptical leads 84 connect each pair of input/output couplings 83 with a transmitter/processor/controller unit (not shown). The components operate in the same manner as those of the structures shown in the preceding figures. By use of this device, an image of the breast can be formed and neoplastic tissue detected, without squeezing the breast or displacing the neoplastic tissue. The type, location, and extent of any neoplastic tissue in the breast can thereby be precisely defined and mapped. Once the neoplastic tissue is precisely mapped, electromagnetic radiation of a selected wavelength or wavelength band is directed to the neoplastic tissue to destroy the tissue without surgery and without damaging the adjacent healthy tissue.

Figure 10A:
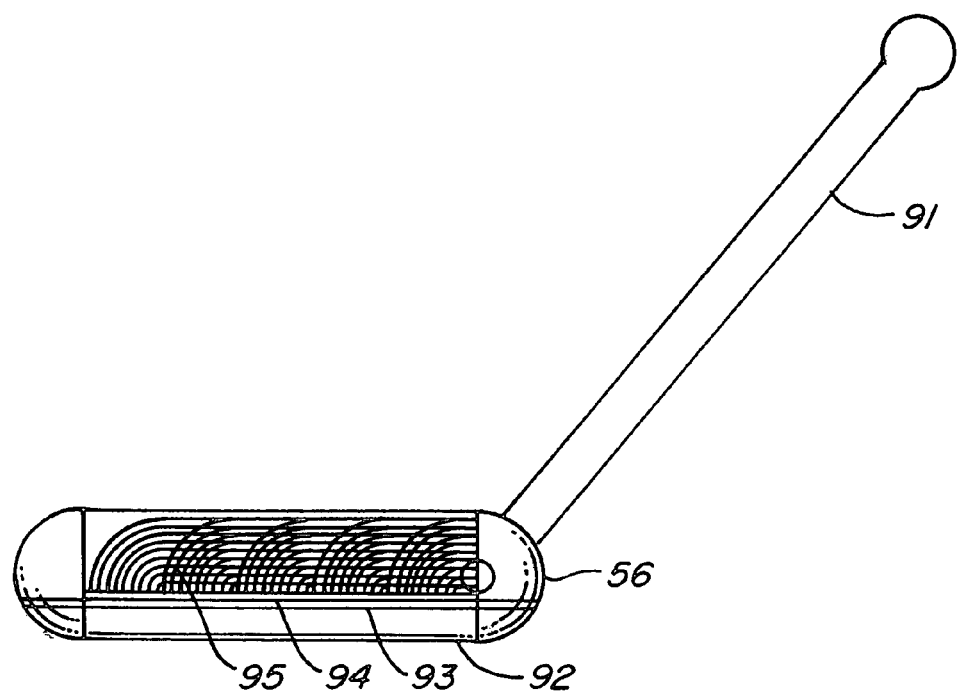
FIG. 10A is a side view of an optical wand that is one of the components of the device of FIG. 7.
Figure 10B:
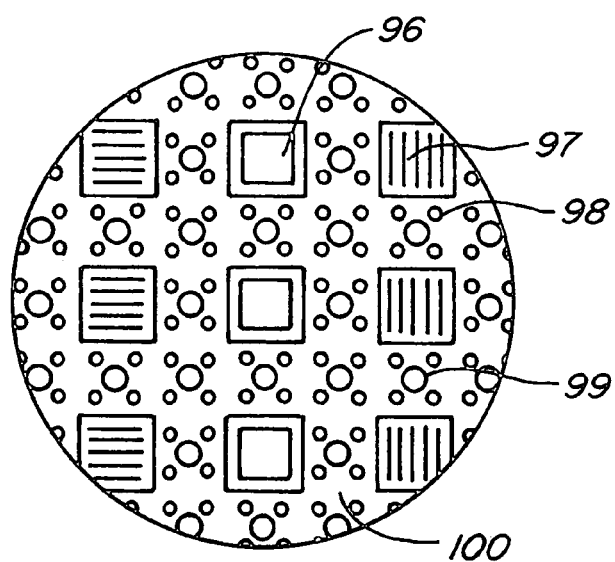
FIG. 10B is an enlargement of a cross section of the optical head of the wand showing the optical components.

FIG. 10A is a side view of the optical head 56 and optical wand 55 of FIG. 7. The optical head 56 is mounted at the end of a swivel handle 91, and the layers on the optical head are a lens 92, a series of interlaced input/output couplings 93, an array of optical components 94, and positive and negative electric leads 95. FIG. 10B is an enlargement of the optical component array of FIG. 10A. The optical components include focal plane arrays 96, microbolometers 97, low power emitting and receiving fiber optics 98, high power emitting fiber optics 99, and CCD detectors 100.

What is claimed is:

1. A method for selectively killing a neoplastic skin lesion in a living organism, where said neoplastic skin lesion is a member selected from the group consisting of dermatofibroma, seborrhoeic keratosis, actinic keratosis, keratoacanthoma, basal cell carcinoma, squamous cell carcinoma, nevus intradermalis, nevus compositus, dysplatic nevus, and lentigo maligna, said method consisting essentially of irradiating at least a portion of said living organism in which said tissue resides with electromagnetic radiation of a wavelength that is non-ionizing and that is absorbed preferentially by said neoplastic tissue relative to adjacent tissue, said preferential absorption due to spectral differences between (i) proteins and lipids of neoplastic tissue and (ii) proteins and lipids of normal tissue, at a sufficient intensity and for a sufficient duration that said neoplastic tissue is killed by heat generated by said radiation without substantial killing of said adjacent tissue.

2. The method of claim 1 wherein said wavelength is within a range selected from the group consisting of 1510-1610 nm, 1040-1070 nm, and 3006-3400 nm.

3. The method of claim 1 wherein said electromagnetic radiation is of a magnitude and duration sufficient to cause said neoplastic skin lesion to rise in temperature to a target temperature of from about 75° C. to about 90° C. without causing said surrounding tissue to reach said target temperature.

4. The method of claim 1 wherein said irradiating is achieved by conveying said radiation to a treatment site within said living organism through a member selected from the group consisting of fiber optics, light pipes and wave guides inserted into said organism.

5. A method for selectively killing neoplastic tissue in a living organism, said method consisting essentially of irradiating at least a portion of said living organism in which said tissue resides with electromagnetic radiation of a wavelength of approximately 265 nm for a sufficient duration that said neoplastic tissue is killed by heat generated by said radiation without substantial killing of said adjacent tissue.

* * * * *